US009040284B2

(12) United States Patent
Buchanan et al.

(10) Patent No.: US 9,040,284 B2
(45) Date of Patent: *May 26, 2015

(54) SYSTEMS AND METHODS OF SAMPLE PROCESSING AND TEMPERATURE CONTROL

(71) Applicant: DAKO Denmark A/S, Glostrup (DK)

(72) Inventors: Kristopher Buchanan, Ft. Collins, CO (US); Marc Key, Ojai, CA (US); John Favuzzi, Santa Barbara, CA (US); Rosanne Welcher, Ventura, CA (US); Benno Guggenheimer, Fort Collins, CO (US); Robert Clark, Loveland, CO (US); Michael Barber, Fort Collins, CO (US); Bob Lathrop, San Jose, CA (US)

(73) Assignee: DAKO DENMARK A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/625,115

(22) Filed: Sep. 24, 2012

(65) Prior Publication Data
US 2013/0084567 A1 Apr. 4, 2013

Related U.S. Application Data

(63) Continuation of application No. 10/539,562, filed as application No. PCT/US03/40880 on Dec. 22, 2003, now Pat. No. 8,298,815.

(60) Provisional application No. 60/435,601, filed on Dec. 20, 2002.

(51) Int. Cl.
*G01N 35/00* (2006.01)
*G01N 1/30* (2006.01)
*G01N 1/31* (2006.01)

(52) U.S. Cl.
CPC ............ *G01N 35/00732* (2013.01); *G01N 1/30* (2013.01); *G01N 1/312* (2013.01);
(Continued)

(58) Field of Classification Search
CPC .......... G01N 35/0095; G01N 35/0092; G01N 2035/0094; G01N 2035/00326; G01N 2035/00306
USPC ........... 435/283.1, 286.2, 286.4, 286.5, 287.2
See application file for complete search history.

(56) References Cited

U.S. PATENT DOCUMENTS 5,573,727 A * 11/1996 Keefe ............................... 422/63
5,578,270 A * 11/1996 Reichler et al. ................. 422/67
(Continued)

FOREIGN PATENT DOCUMENTS

CA 2172363 3/1995
WO WO93/20440 10/1993

*Primary Examiner* — Nathan Bowers
(74) *Attorney, Agent, or Firm* — Finnegan, Henderson, Farabow, Garrett & Dunner LLP.

(57) ABSTRACT

Systems and methods of sample processing and temperature control are disclosed. The invention may especially relate to temperature control, and may in some embodiments be methods of temperature control of an automated sample processing system and methods of automated sample processing. Specifically, the present invention provides temperature control in relation to sample processing systems and methods of processing samples, and in some embodiments provides temperature control in relation to sample carriers and processing materials such as reagents. Corresponding systems and devices are disclosed, including sample processing systems (1), sample carrier temperature regulation systems (60), reagent temperature regulation systems, sample processing control systems, and temperature regulation devices, among other embodiments. Scientific fields to which the present invention may have particular applicability include immunohistochemistry, hybridization, fluorescent in-situ hybridization, special staining, such as special staining of histological samples, microarray sample processing, and cytology, as well as potentially other chemical and biological applications.

20 Claims, 14 Drawing Sheets

(52) U.S. Cl.
CPC ...... *G01N35/00871* (2013.01); *G01N 35/0092* (2013.01); *G01N 35/0099* (2013.01); *Y10T 436/114998* (2015.01); *Y10T 436/113332* (2015.01); *Y10T 436/2575* (2015.01); *Y10T 436/112499* (2015.01); *Y10T 436/25* (2015.01); *Y10T 436/11* (2015.01); *Y10T 436/114165* (2015.01); *G01N 35/00712* (2013.01); *G01N 2035/00039* (2013.01); *G01N 2035/00089* (2013.01); *G01N 2035/00326* (2013.01); *G01N 2035/00366* (2013.01); *G01N 2035/00376* (2013.01); *G01N 2035/00435* (2013.01); *G01N 2035/00881* (2013.01); *G01N 2035/00891* (2013.01); *G01N 2035/00306* (2013.01); *Y10S 901/02* (2013.01); *Y10S 901/41* (2013.01)

(56) References Cited

U.S. PATENT DOCUMENTS

| | | | |
|---|---|---|---|
| 6,096,561 | A * | 8/2000 | Tayi ............................ 436/518 |
| 2003/0099573 | A1 * | 5/2003 | Tseung et al. ................. 422/63 |

* cited by examiner

IHC Deparaffinization Process:

| Process | Protocol Step | Time (min) | Temp C | Waste Segregation |
|---|---|---|---|---|
| Deparaffinization | Switch | | | Hazardous Waste |
| | Histoclear | 5 | | |
| | Drain | | | |
| | Histoclear | 5 | | |
| | Drain | | | |
| Re-Hydration | 100% Ethanol | 5 | | |
| | Drain | | | |
| | 100% Ethanol | 5 | | |
| | Drain | | | |
| | 95% Ethanol | 5 | | |
| | Drain | | | |
| | 95% Ethanol | 5 | | |
| | Rinse - Water | 5 | | |
| | Switch | | | Non-Hazardous Waste |
| Target Retrieval | Target Retrieval | 20 | 95 | |
| | Target Retrieval Cool | 20 | 55 | |
| | Rinse - Water | 5 | RT | |
| Enzyme/Antibody Application | Peroxide Block | 5 | | |
| | Enzyme Pretreatment | 5 | | |
| | Rinse - Buffer | | | |
| | Pre-Diluted Antibody | 10 | | |
| | Rinse - Buffer | | | |
| | EnVision-HRP | 10 | | |
| Chromogen/ Counterstain Treatment | Rinse - Buffer | | | |
| | Switch | | | Hazardous Waste |
| | DAB | 5 | | |
| | Rinse - Buffer | | | |
| | Hematoxylin | 5 | | |
| | Rinse - Water | | | |

Fig. 8

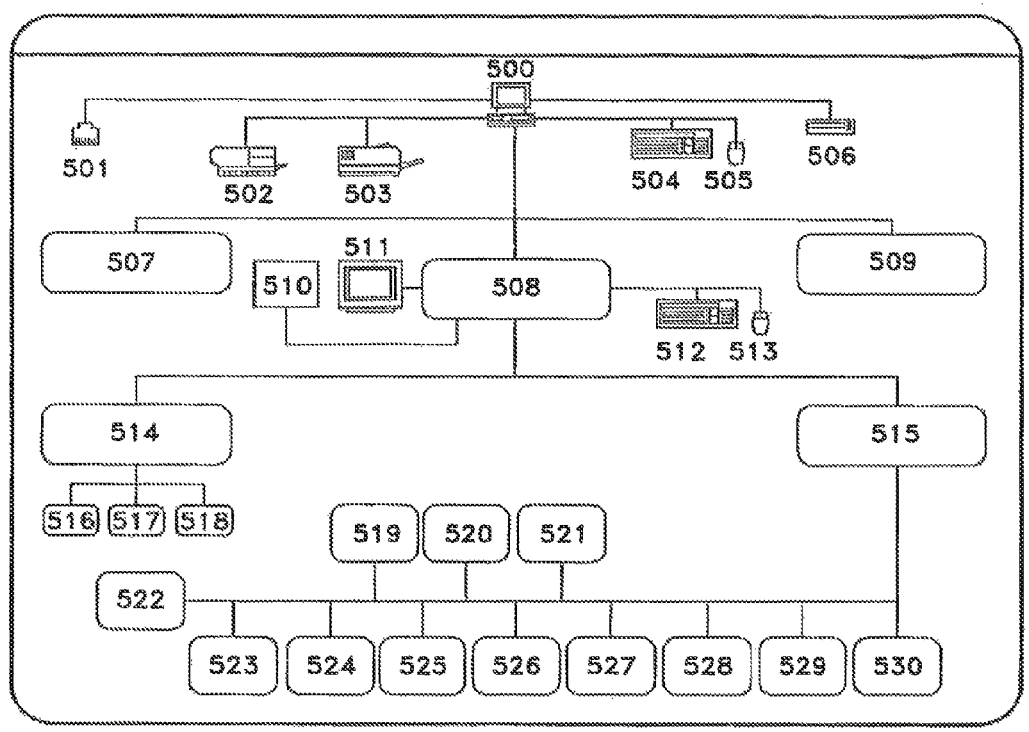

Key to Figure 9

500 Manager
501 100 BaseT
502 Laser printer
503 Label Printer
504 Keyboard
505 Mouse
506 Storage Media
507 Stainer A Embedded PC
508 Stainer B Embedded PC
509 Stainer C Embedded PC
510 Touch Screen
511 Monitor
512 Keyboard
513 Mouse
514 Motor Controller
515 Master PCBA
516 X-Axis
517 Y-Axis
518 Z-Axis
519 LCD Touch
520 Probe Wash/Swap
521 Misc PCBA
522 Cart PCBA
523 Drawer 1 Control
524 Drawer 2 Control
525 Drawer 3 Control
526 Drawer 4 Control
527 Drawer 5 Control
528 Drawer 6 Control
529 Drawer 7 Control
530 Drawer 8 Control

Fig. 9

SYSTEMS AND METHODS OF SAMPLE PROCESSING AND TEMPERATURE CONTROL

This application a continuation of application Ser. No. 10/539,562, filed Jun. 17, 2005, which is the United States National Stage of International Application No. PCT/US2003/040880, filed Dec. 22, 2003 which claims the benefit under 35 U.S.C. 119(e) of U.S. Provisional Application No. 60/435,601 filed Dec. 20, 2002, each hereby incorporated by reference.

TECHNICAL FIELD

The present invention is directed to the field of sample processing. Embodiments of the invention may especially relate to temperature control. Specifically, the present invention relates to temperature control in relation to sample processing systems and methods of processing samples, and may be directed to sample processing in relation to sample carriers and processing materials such as reagents. Scientific fields to which the present invention may have particular applicability include immunohistochemistry, in-situ hybridization, fluorescent in-situ hybridization, special staining, such as special staining of histological samples, microarray sample processing, and cytology, as well as potentially other chemical and biological applications.

BACKGROUND OF THE INVENTION

Sample processing in chemical and biologic analyses, such as immunohistochemical (IHC) applications, may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

The sample processed may be any material, but is most likely a biologic material such as a biological sample or a biological specimen, perhaps such as a histological sample, e.g. tissue and cell specimens, cells, collections of cells, or tissue samples, the definition to include cell lines, proteins and synthetic peptides, tissues, cell preps, cell preparations, blood, bodily fluids, bone marrow, cytology specimens, blood smears, thin layer preparations, and micro arrays. It should also be understood to include slide-based biological samples. In preparation for biologic sample analysis, for example, a biological sample may be acquired by known sample acquisition techniques and may comprise, for example in immunohistochemistry (IHC) applications, tissues generally or even in some applications one or a plurality of isolated cells, such as in microarray samples, and may be presented on a sample carrier such as a microscope slide. Furthermore, the sample may be presented on the carrier variously and potentially in some form of preservation. As one example, a sample such as a layer or slice of tissue may be preserved in formaldehyde and presented on a carrier with one or more paraffin or other chemical layers infiltrating the sample.

IHC applications, for example, may require processing sequences or protocols that comprise steps such as deparaffinization, target retrieval, and staining, especially for in-situ hybridization (ISH) techniques. Important for many IHC applications, and many sample processing sequences and protocols, generally, are temperature characteristics associated with the sample, sample carrier, and the processing environment. As but one example, stains such as histochemical reagents are typically used to identify various histological features. The reagents may employ antibodies, for example, that bind to specific proteins of the sample. In many processes, a need can exist for adequate control of processing characteristics such as temperature. In regard to staining, it should be understood that the term staining can reference the end product of the process, by which certain parts of the sample may be stained, i.e. have obtain a different color, either in the optic range or in another electromagnetic range, such as ultra violet. Staining may be detectable, perhaps automatically detectable, through some change in properties, such as fluorescent properties, magnetic properties, electrical properties or radioactive properties. Staining a sample can involve a series of treatment steps, such as washing, binding of reagents to the specific parts of the sample, activation of the reagents, etc. Sample processing with the reagents may require the addition and removal of reagents in accordance with a defined protocol that may include a defined temperature.

Traditional sample processing technology has provided temperature control through heating devices that heat an entire set of sample carriers in the sampling processing system. Other technologies, such as the sample processing system described in U.S. Pat. No. 6,183,693, may provide heating devices for individual sample carriers that are individually controlled to heat the slides. However, each of these traditional sample processing systems may lack a desired degree of temperature control or temperature tolerances.

Inadequacies in temperature control of traditional technologies may include uncontrolled cooling. Traditional systems may only provide ambient cooling when the heating devices are off. Ambient cooling is not considered active control and may not meet protocol temperature requirements or may not otherwise be optimal. Although healing and heat control may be features of such systems, controlled cooling of the samples, sample carriers, and processing environments may not always be adequately addressed. Cooling techniques such as hooded fans may be incorporated in some traditional technologies. However, these devices can lack sufficient capabilities of temperature control to meet certain protocol requirements, especially temperature tolerances for samples, sample carriers, reagents, and ambient system temperature.

Traditional systems may even lack temperature control, perhaps as related to temperature tolerances generally, as such tolerances may not be adequately maintained during ambient or other traditional cooling, or during processing sequences or events, generally. In some protocols, for example, the temperature tolerances during non-heating periods may be such that uncontrolled temperature changes may produce undesirable results during the processing sequence. Other IHC processes of the protocol may be adversely affected by uncontrolled temperature changes, the degree of temperature change, and temperature changes outside of preferred tolerances. The lack of temperature control may actually dissuade technologists from employing preferred processing sequences or protocols, especially IHC sequences that may be dependent upon a particular temperature tolerance and the amount of temperature change during a processing sequence.

Certain types of temperature control may not have even been addressed in traditional sample processing system technologies. As previously mentioned, reagents can play a vital role in the staining sequence of many processing protocols. The quality of the reagents, therefore, may be important for adequate sample processing. Reagents, for example, can have a certain shelf life that may be limited if maintained at undesirable temperatures such as the typical ambient temperatures of traditional processing systems and the laboratories housing such systems. Traditional technologies may lack the temperature control needed to optimally preserve the reagents stored in the processing system that are often subject to inadequate or changing ambient temperatures of such systems and the laboratory environment.

Previously, in some traditional processing sequences, protocol steps may have been performed manually, potentially creating a time-intensive protocol and necessitating personnel to be actively involved in the sample processing. Attempts have been previously made to automate sample processing to address the need for expedient sample processing and a less manually burdensome operation. However, such previous efforts may have not fully addressed the needs for an automated sample processing system. Previous efforts to automate sample processing may be especially deficient in several aspects that prevent more robust automated sample processing, such as: the lack of sufficient temperature control and temperature monitoring associated with sample processing, and the lack of real-time, lack of active, or lack of adaptive temperature control capabilities for multiple sample batch processing. As but one example, the lack of controlled cooling features of traditional systems may require longer wait times for the technologist during processing sequences to allow samples, sample carriers, and ambient temperatures to reach certain protocol temperatures.

The above-mentioned drawbacks or inadequacies of traditional sampling techniques may also be applicable to other chemical and biologic analyses beyond those examples previously described.

Past efforts at automated sample processing for samples presented on carriers such as slides, such as U.S. Pat. No. 6,352,861 and U.S. Pat. No. 5,839,091 have not afforded the various advantages and other combinations of features as presented herein.

DISCLOSURE OF THE INVENTION

Sample processing and temperature control can be accomplished to address the inadequacies of previous sample processing technology. The sample processing and temperature control features of the present invention are addressed in a fashion that may provide the processing of one or more batches of samples and carriers with common protocols or of a plurality of groups of one or more samples and carriers having differing processing protocols. Processing may in a occur sequential or non-sequential fashion. Processing of samples and temperature control may be determined by the protocol to be followed for each sample or a protocol for multiple samples. Aspects of the present invention may be especially applicable to sample processing having one or a plurality of processing steps to be performed on one, a portion, or an entirety of samples. Protocols may include certain temperature tolerances for samples and system components such as samples, carriers, or reagents. There may be temperature tolerances that may be necessary for some sample processing sequences. Aspects of the present invention may be especially applicable to IHC techniques, as well as in-situ hybridization (ISH) and fluorescent in-situ hybridization (FISH), special staining of histological samples, and microarrays; and especially techniques, generally, incorporating deparaffinization and/or target retrieval and/or the staining of samples. Furthermore, embodiments may be especially directed to processing sequences addressing issues of temperature control and data acquisition related thereto.

To achieve the foregoing and other objects of invention, the invention may comprise an automated sample processing system comprising a sample processing control system and a temperature regulation system or element, such as a temperature regulation device, that may be responsive to a sample processing control system. The temperature regulation device in some embodiments may actively regulate temperature, perhaps even corresponding to at least one protocol tolerance. In some embodiments it may comprise an adaptive sample processing control system. The invention may actively regulate temperature, including actively reducing temperature, and may adaptively control temperature, again including reducing temperature.

Embodiments of the invention may further comprise: regulating temperature, such as for a substance or within protocol or other tolerances; actively regulating temperature and even reducing temperature; controlling reduction of temperature; ramping temperature up or down; providing at least one sample, determining a processing sequence for it, determining at least one temperature tolerance, and actively regulating temperature corresponding to the tolerance.

Embodiments of the invention addressing temperature control may comprise: sample carrier temperature regulation systems; sample carrier temperature regulation systems configurable with one or a plurality of sample carrier supports; and corresponding methods of sample carrier temperature regulation. Embodiments may also include: reagent temperature regulation systems; reagent temperature controls; conductive reagent temperature regulation systems; and corresponding methods of reagent temperature regulation.

In some embodiments, an automated sample processing system is disclosed comprising a plurality of drawers, a plurality of sample carrier retainment assemblies each removably configured with one of the drawers, a temperature regulation system, such as a temperature regulation device, and an adaptive sample processing control system to which the drawers, the sample carrier retainment assemblies, and the temperature regulation system may be responsive. An adaptive sample processing control system may automate the sample processing system such that one or more batches of samples may be adaptively processed according to one or more protocols, especially accordingly to temperature requirements of the protocol(s), potentially indicated by information on the slides that may be automatically identified by the sample processing control system perhaps through a camera or the like. Sample processing may comprise one or more sampling protocols and steps, such as deparaffinization, target retrieval, and staining, and the temperature requirements for each, such as their temperature tolerances.

As mentioned, sample processing temperature may be achieved to adequately maintain or change temperatures within protocol tolerances. Accordingly, in some embodiments, temperatures of the sample, sample carrier, or ambient system temperature, or combinations thereof, can be changed in a controlled fashion to achieve ramping temperature increases and decreases (and thus considered as having a temperature ramp up element or a temperature ramp down element, respectively), can have preferred tolerances, can minimize changes of temperature during processing, can maintain reagent quality through temperature control of the reagents, can provide for adaptive heating or cooling, and can control temperatures below or above ambient system or even the ambient lab environment temperature.

Temperature sensing, such as Infrared (IR) or other temperature sensing, may be accomplished in some embodiments, perhaps even by a camera or perhaps a photodiode device. Temperature information, such as ambient system temperature, slide temperature, sample temperature, and reagent temperature, may be identified, and in some preferred embodiments, instantaneously identified. In some embodiments, protocol information, such as required temperature, and required temperature tolerances may be provided. The system may include an adaptive sample processing control system or an adaptive temperature regulation element. An adaptive temperature element may include a system that alters or causes a change in the degree or nature of control due to changes in an another component. But one example may be a system that monitors or adjusts temperature more frequently in certain situations, perhaps such as when ambient and desired temperatures have a large spread—perhaps greater than 5 or 10 degrees C.—or such as when there is an unusual change in ambient—here perhaps a change of more than 3 or 5 degrees C. The sample processing system may process one or more slides, or one or more batches of slides, concurrently, sequentially, or in any other temporal fashion, potentially in accordance with temperature protocol information provided by a slide having a sample or provided by the adaptive sample processing control system. Sample batches or individual slides may be inserted or removed during processing protocol steps by the control and monitoring accomplished by the adaptive sample processing control system.

Another embodiment of the present invention may comprise a method of sample processing, comprising the steps of: accessing at least one of a plurality of samples or perhaps drawers, providing at least one sample carrier retainment assembly configured with at least one sample carrier, configuring at least one of the drawers with the at least one sample carrier retainment assemblies, utilizing a carrier temperature regulation element and adaptively or actively controlling temperature during processing of the sample carriers. Any aspect of temperature control disclosed herein may of course be combined with any element or elements of such disclosed sample processing systems, or with any of the disclosed features or steps of sample processing.

Many other embodiments of the invention are disclosed in this application, some of which may comprise independently, dependently, or in combination, sample processing systems, environmental control systems, and any of the various other systems, devices, apparatus, assemblies, steps, and features disclosed herein or in the incorporated references of this application. In addition, the various method steps may be provided for individual samples or multiple batch processing, sample diagnostic features, and real-time or adaptive capabilities for multiple batch processing.

BRIEF DESCRIPTION OF THE FIGURES

The accompanying figures illustrate some of the preferred embodiments of the present invention, and together with the written disclosures of the specification and claims, if any, facilitate an understanding of the disclosed embodiments.

FIG. 8 is a chart providing description of representative deparaffinization, target retrieval and other steps of an embodiment of the invention.

FIG. 9 is a depiction of a networked embodiment connecting one stainer with one manager and one label printer.

MODES FOR CARRYING OUT THE INVENTION

The following descriptions are provided to describe various embodiments of the present invention to facilitate an understanding of the invention. The variously described embodiments should not be construed to limit the present invention to only explicitly described embodiments. Those embodiments and combinations of features inherent in this disclosure or otherwise known to one skilled in the art are also disclosed as the present invention. This description may further be understood to disclose the variously described embodiments of systems, methods, techniques, and applications, both singularly and in various combinations, consistent with the various features of the present invention. Accordingly, the following is a detailed description of a number of specific embodiments of the invention.

Figure 1:
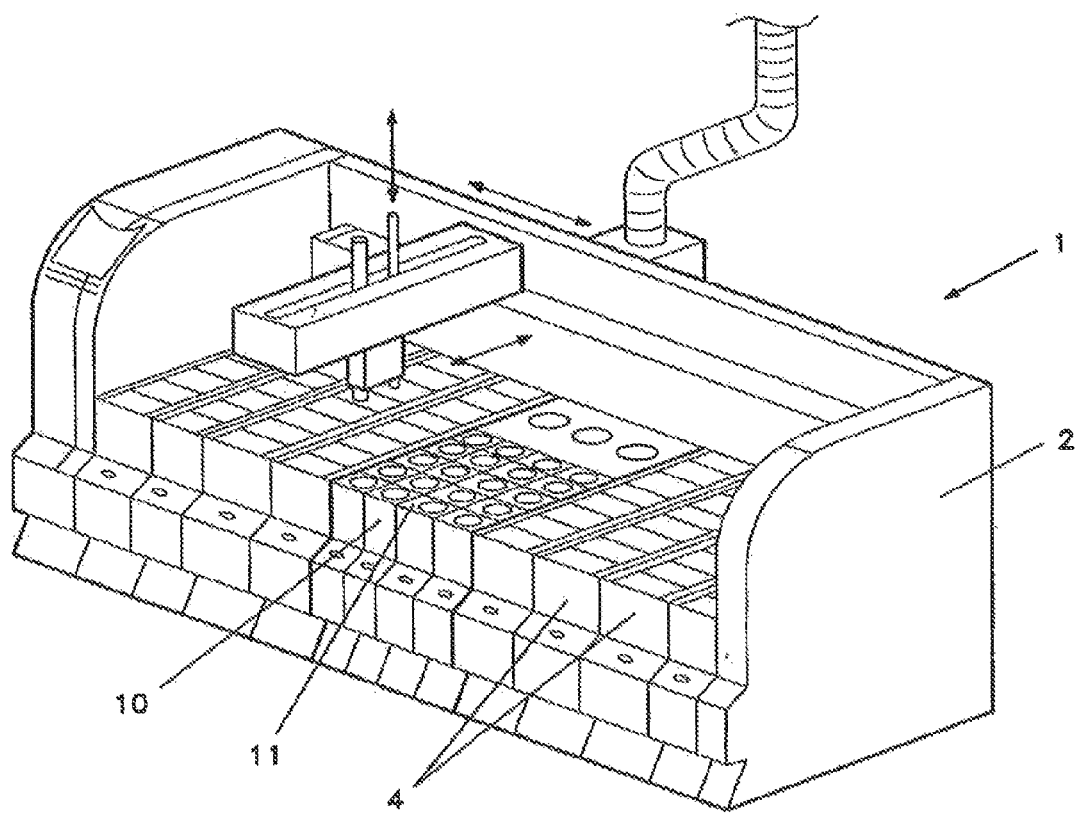
FIG. 1 is a isometric perspective view of an embodiment of an overall system incorporating some of the features of the invention.
Figure 10:
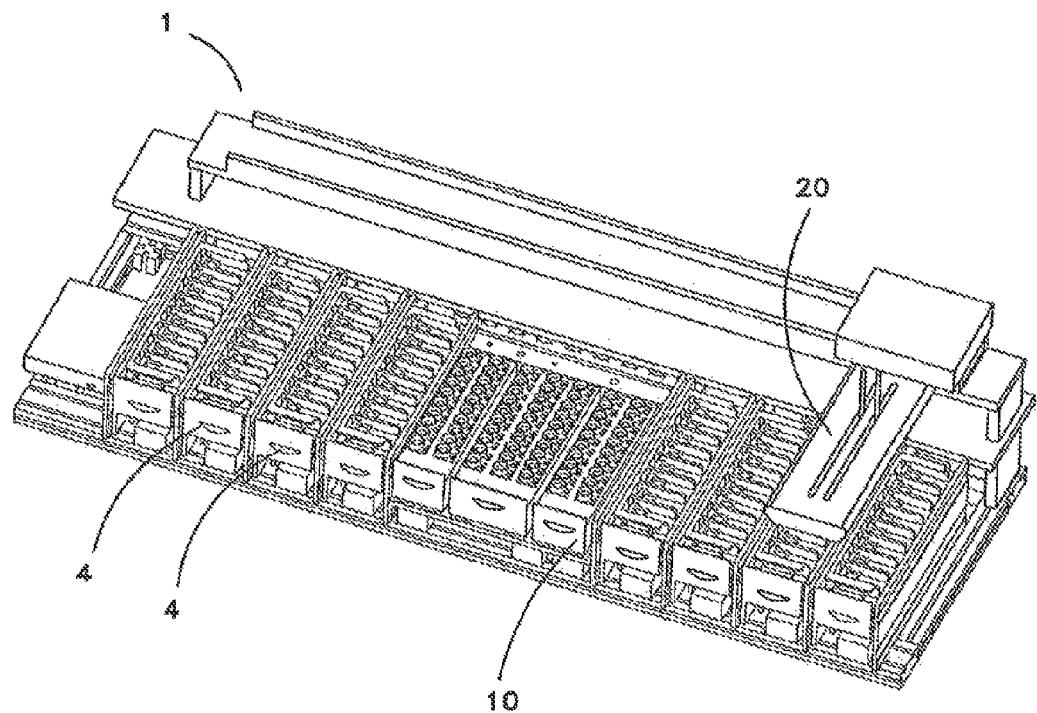
FIG. 10 is a depiction of an embodiment for processing a collection of samples with a collection of reagents according to the invention.

FIGS. 1 and 10 show embodiments of a sample processing system 1 in accordance with the present invention. Cabinet sections 2 form outer portions of the system and serve to address general structural considerations of the system (a top cabinet section is not shown in FIG. 1). The sample processing system may comprise a plurality of drawers 4 used for the handling and processing of samples and sample carriers such as slides, potentially microscope slides. Other sample carriers may be accommodated consistent with the present invention. Each drawer may be configured to accommodate sample carrier retainment assemblies, such as slide retainment assemblies, carrier racks, modules, or magazines.

Figure 2:
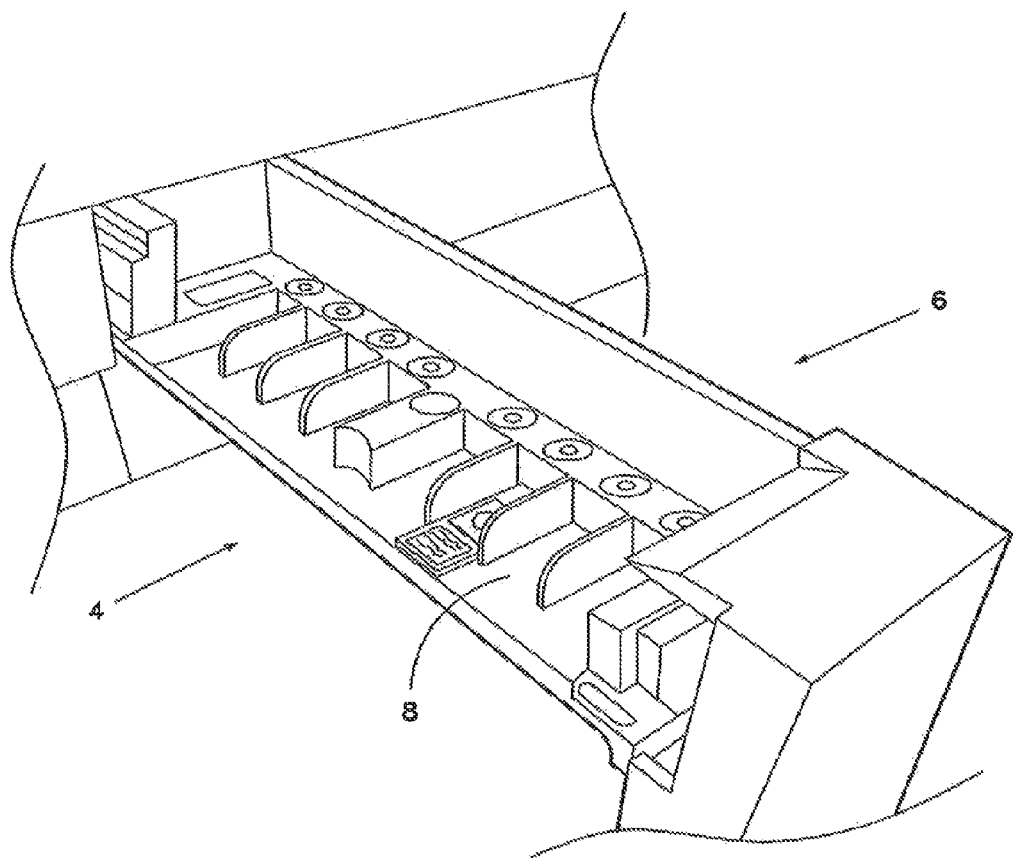
FIG. 2 is an elevated view of an embodiment of a portion of a sample carrier retainment assembly of one embodiment of the invention.

One embodiment of a sample carrier retainment assembly may comprise a slide retainment assembly 6 as shown in FIG. 2. The slide retainment assembly may comprise a slide rack, module, or magazine. Slide retainment assembly 6 is configured to accommodate a plurality of slides (only one is shown) in at least one configuration in corresponding sample carrier retention devices 8. The sample carrier retainment assemblies are utilized in the processing of samples as further described below. It should be further noted that the sample carrier retainment assembly can be removably configured with the drawers 4, and may be stackable or nested within other retainment assemblies.

One or more drawers 10 as shown in FIG. 1 may be provided to accommodate processing materials such as reagent containers for sample processing. A processing material retainment assembly, such as a container rack 11, shown in FIG. 1, for example, may be utilized to accommodate reagent containers or other processing materials within each of drawers 10. Bottle inserts may be preferably configured with the retainment assembly to ensure proper processing material positioning within the processing material retainment assembly and the drawer.

Multiple drawers 4 as shown in FIG. 1, allow for one or a plurality of sample processing protocols to be performed by the system 1. Past efforts at sample processing may have been limited to processing sequences for an entire batch of carriers within the system. The present invention, however, in part by providing a plurality of drawers and carrier retainment assemblies, may allow for multiple batch processing, including real-time alteration capabilities for multiple batch processing, as further described below.

Figure 3:
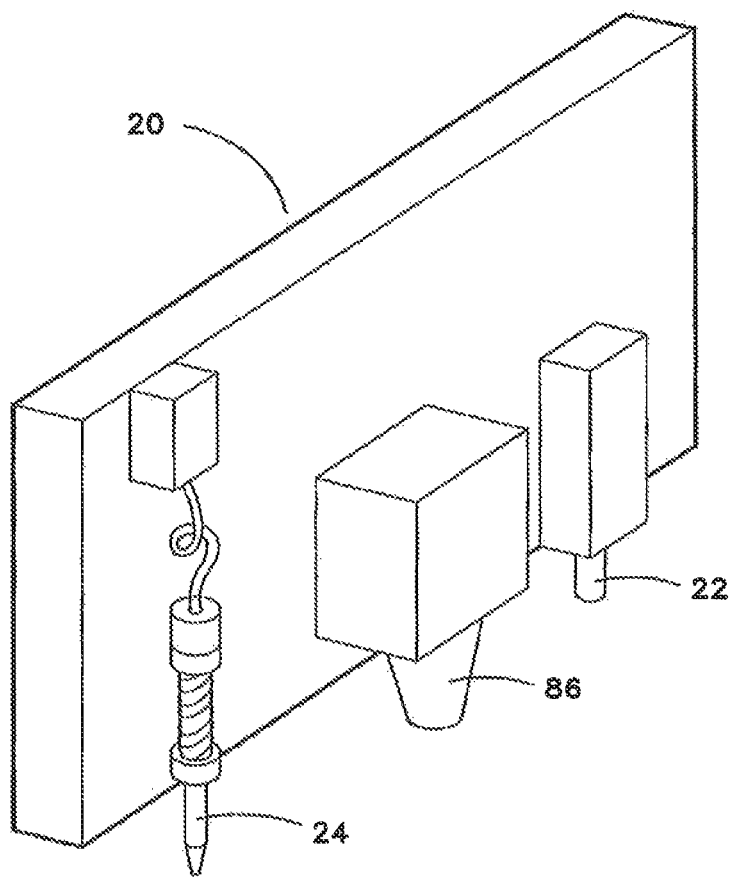
FIG. 3 is a perspective view of an embodiment of a robotic movement aspect of one embodiment of the invention.
Figure 4:
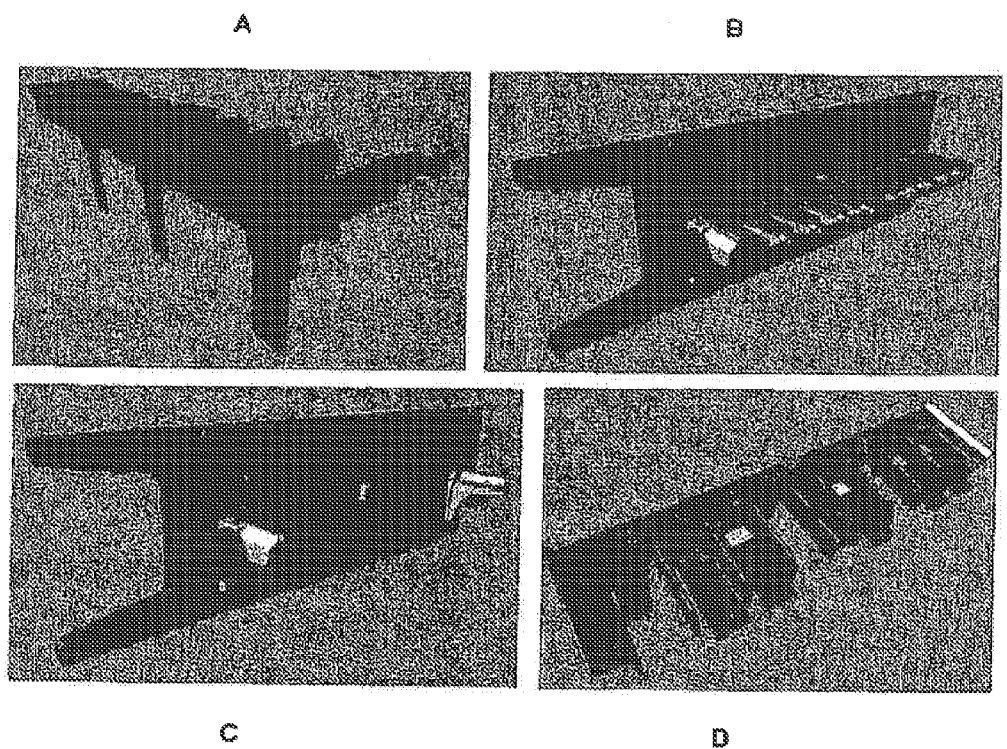
FIGS. 4A-D are views of embodiments of sample carrier retainment assembly aspects of one embodiment of the invention.

Embodiments of the present invention may further comprise an arm 20, shown in FIG. 3, utilized in sample processing, potentially having robotic movement, and in some embodiments, Cartesian movement. The arm 20 may comprise one or more elements, such as an actuator probe 22, a probe such as a syringe 24, a sensor element, an optical sensor 86 (including but not limited to a camera or a CCD device), and even a non-discrete volume fluid and/or air applicator. The optical sensor may even be configured to sense temperature such as through IR detection or the like.

In accomplishing a processing sequence, and in some preferred embodiments of the present invention, slides may be configurable in both vertical and horizontal positions such as for the pretreatment and/or staining processes, as shown in FIGS. 4A-4D. This may allow for the automation of the pretreatment and staining of slides in various manners. The slides may be initially loaded onto the carrier retention assemblies, such as slide racks, and drawers in the horizontal position. The slides may be horizontally supported by adjustable carrier supports. If pretreatment is required, such as deparaffinization, the system may rotate the slide into the vertical position and may lower these samples into a processing tank which may be maintained at a desired temperature such as perhaps 95 degrees C. and may be filled with the required fluids. In some embodiments, the slide rack may be lowered to affect lowering of the slides. To perform a staining process on the slides, as described below and in some embodiments, the system may rotate the slide to the horizontal position and a syringe or probe may apply fluid to the sample, providing a horizontal staining of the sample. Each slide can be rotated independently allowing for the independent processing of different samples with different requirements.

The sample processing system may further have the ability to maintain and regulate the internal temperature of the system, including maintaining and regulating the temperature of samples and sample carriers, to specified temperatures, and even within temperature tolerances of certain sample protocols. Controlling temperature can avoid a need to alter protocols for seasonal or other non-optimal temperature variations. Thermal control may be needed for several heat sources within the system and for temperature effects from outside the system, as well as ambient temperature control of the internal environment of the system. In some preferred embodiments, the internal ambient temperature may be maintained at a set point, perhaps about 24° C., and perhaps ±2° C. or ±1° C.; in other embodiments the sample or reagent temperature may be maintained at about a set point, perhaps about 24° C., and perhaps ±2° C. or ±1° C., at about an incremental range, and in some embodiments a non-integer incremental range. Reagents used in the sample processing system can be optimized to operate at a thermal set point for a substance such as a reagent or sample or for the system in general, and in some embodiments, may be optimized for temperature maintenance at less than about the ambient temperature of the system.

As previously mentioned, reagents may play a vital role in the staining sequence of many processing protocols. The quality of the reagents, therefore, may be important for adequate sample processing. In order to maintain shelf life of the reagents of the sample processing system, the reagent temperatures may also be controlled such as by a reagent temperature control element to maintain desirable temperatures, especially respective of typical ambient temperatures of the processing system and temperature effects from outside environments such as typical laboratories environments that may lack appropriate temperature control for the processing system. This may include maintaining the reagent at a temperature specified by the manufacturer, such as between about 2 and about 8 degrees C., so that the manufacturer shelf life is fully maintained and not shortened.

Accordingly, the present invention may comprise an automated sample processing system comprising a temperature regulation system or a temperature regulation device and a sample processing control system to which the temperature regulation system is responsive with perhaps active temperature regulation (e.g., temperature control with both heating and cooling) and even within certain tolerances. It may also be adaptive as mentioned above.

Figure 6:
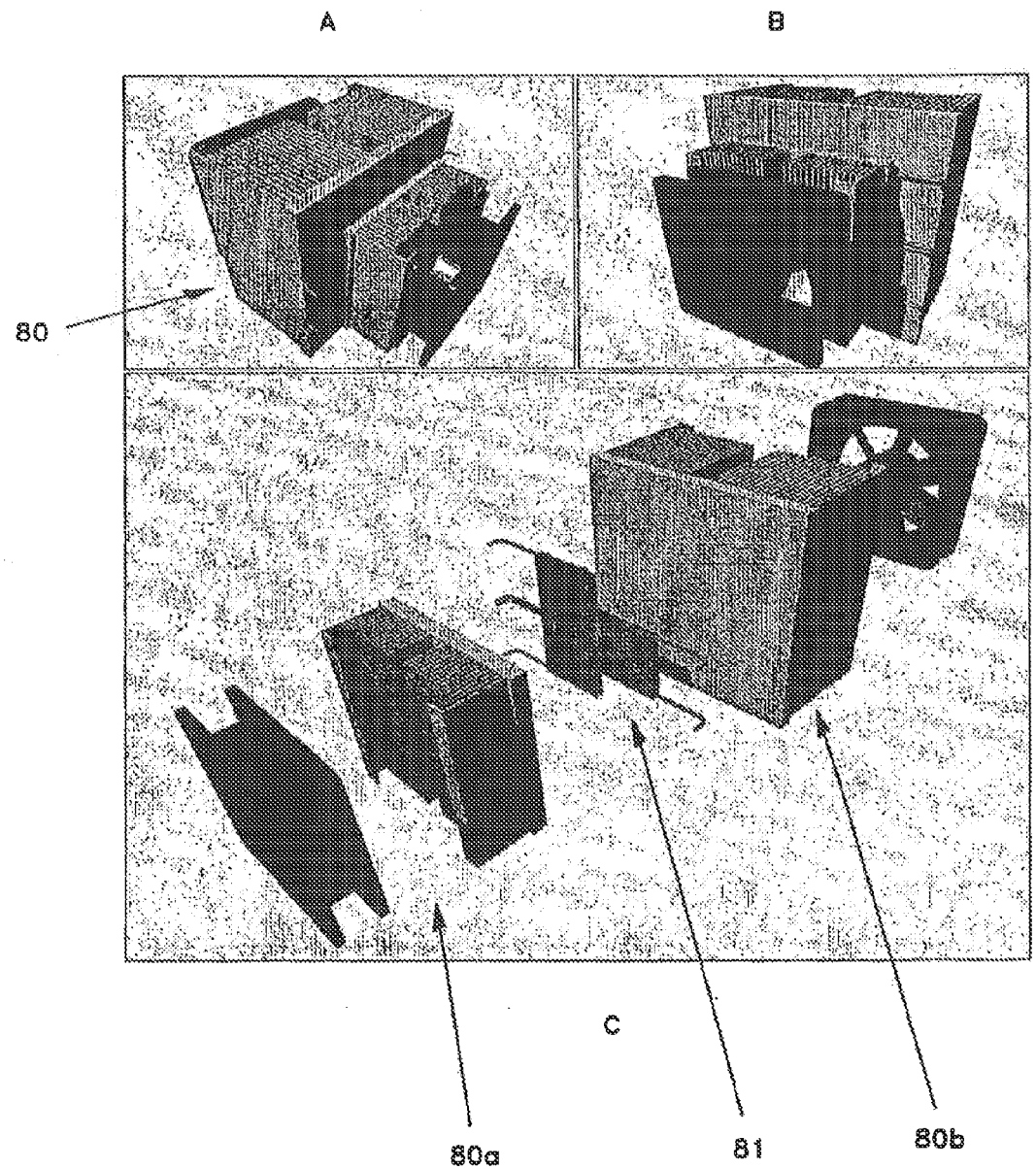
FIGS. 6A-C are additional views of embodiments of temperature control aspects of one embodiment of the invention.

Configurations of the temperature regulation system may include a Peltier device or Peltier temperature control, and in configurations such as shown in FIG. 6, a heat sink/fan pair 80*a* on the inside of the system's temperature-controlled interior volume. The other heat sink/fan of the pair 80*b* may be on the outside of the controlled volume, where it is exposed to the ambient environment of the laboratory. One or more thermoelectric devices (TEDs) 81 perhaps including the electrical junctions themselves may be located on the boundary between the interior and exterior. The TED or TEDs may generate a hot portion and a cold portion and may aid in moving heat into or out of the desired location. The "hot" portion may be configured to distribute heat from the exterior of the controlled interior volume. If the temperature of the "hot" portion of the TED is controlled to maintain a low temperature, such as with a controlled paired heat sink/fan, the corresponding "cold" portion of the TED, may be configured within the controlled interior volume, may be colder by a corresponding amount, and may act in conjunction with a paired heat sink/fan as a controlled refrigerator, and may even actively reduce the temperature of the interior volume, or may achieve protocol tolerances as further described below. Such an item may serve as a temperature reduction element for various locations or purposes as described below.

As mentioned above, the internal temperature of the system may be controlled by an adaptive sample processing control system. Some applications may provide temperatures at 24° C.±2° C.; in other embodiments the internal ambient temperature may be maintained at about 24° C. comprises ± an incremental range, such as a non-integer incremental range. One temperature regulation system of the present invention may comprise one or more heat pumps, and in some preferred embodiments two thermoelectric heat pumps (heat pump 80 shown in FIGS. 6A and 6C). The temperature regulation system may feature each heat pump module having a heat sink and fan on either side of the TED.

Figure 5:
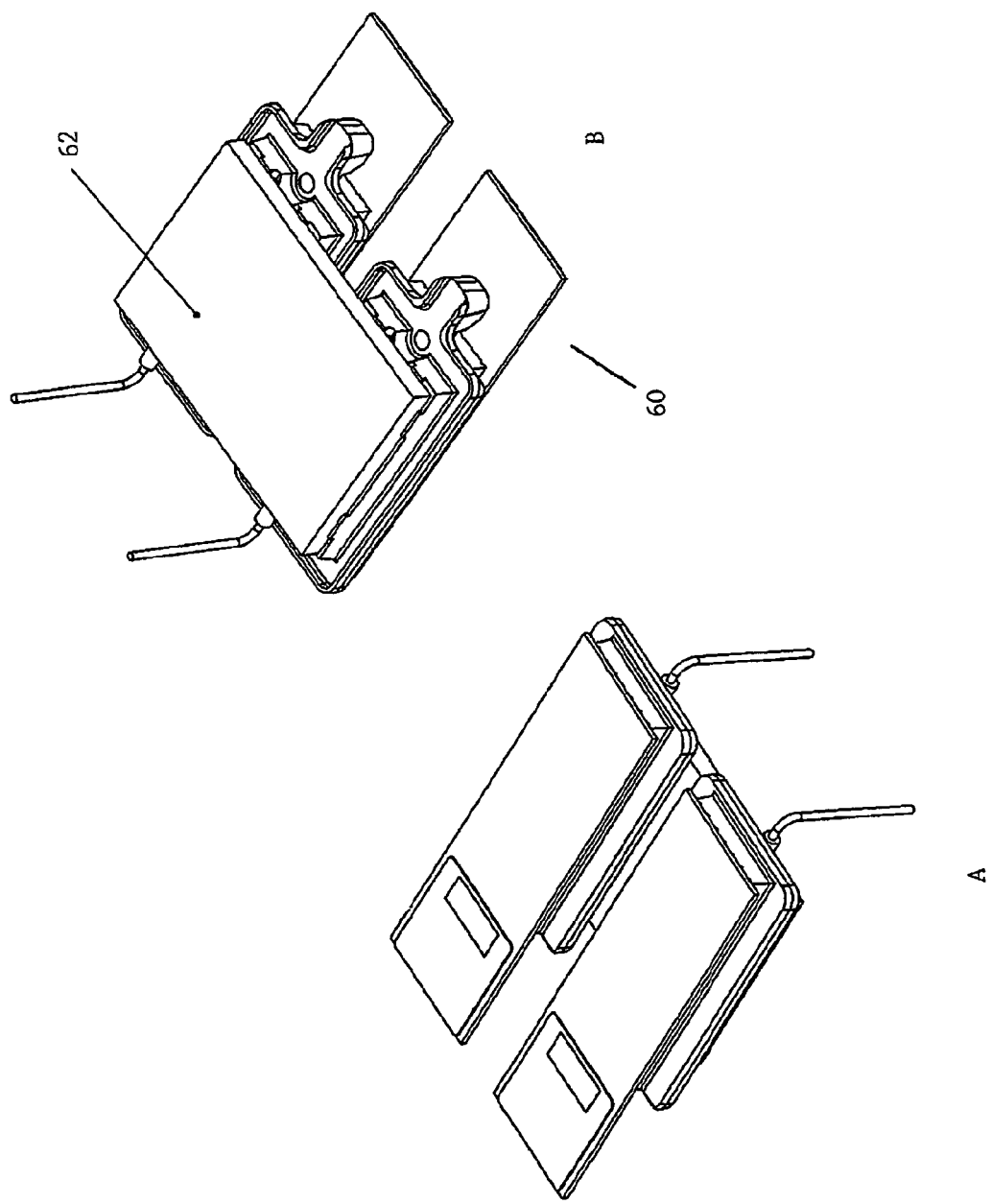
FIGS. 5A-B are views of embodiments of temperature control aspects of one embodiment of the invention.
Figure 11:
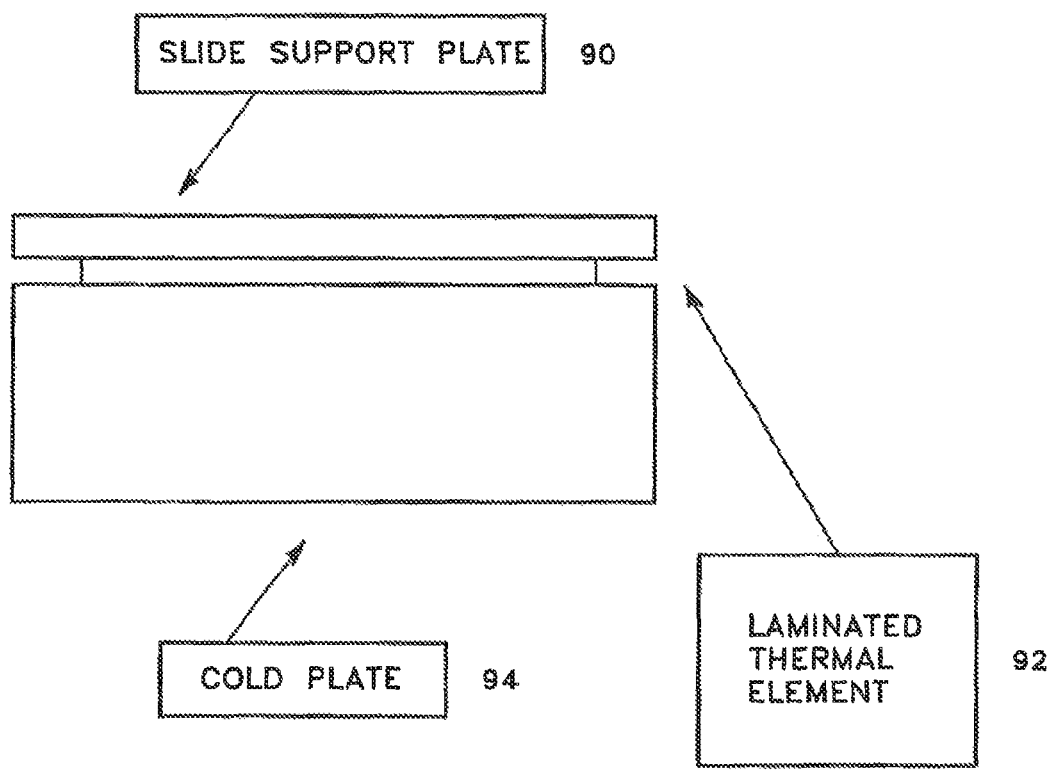
FIG. 11 is a block diagram of a temperature regulation design according to an embodiment of the invention.

Embodiments of the invention may comprise sample carrier temperature regulation systems, in some embodiments sample carrier temperature regulation systems configurable with one or a plurality of sample carrier supports, and corresponding methods of sample carrier temperature regulation. Some embodiments may comprises a Peltier grid, such as grid 60 shown in FIG. 5, that may be used to heat or cool the slides during processing of the samples. Thermal elements 62 may heat the slides, in some embodiments from ambient to about 120° C. comprises in about 3 minutes. Sample carrier temperature regulation systems may comprise, in some embodiments, one or more sample carrier supports such as a slide support plate 90 as shown in FIG. 11, configured with temperature regulation elements, such as one or more temperature regulation elements, and in some embodiments a laminated thermal element 92 as shown in FIG. 11, and a cold plate 94 shown in FIG. 11.

The sample carrier temperature regulation system may reach target temperature even when ambient temperature is about or greater than target temperature, or about or less than target temperature.

Figure 12:
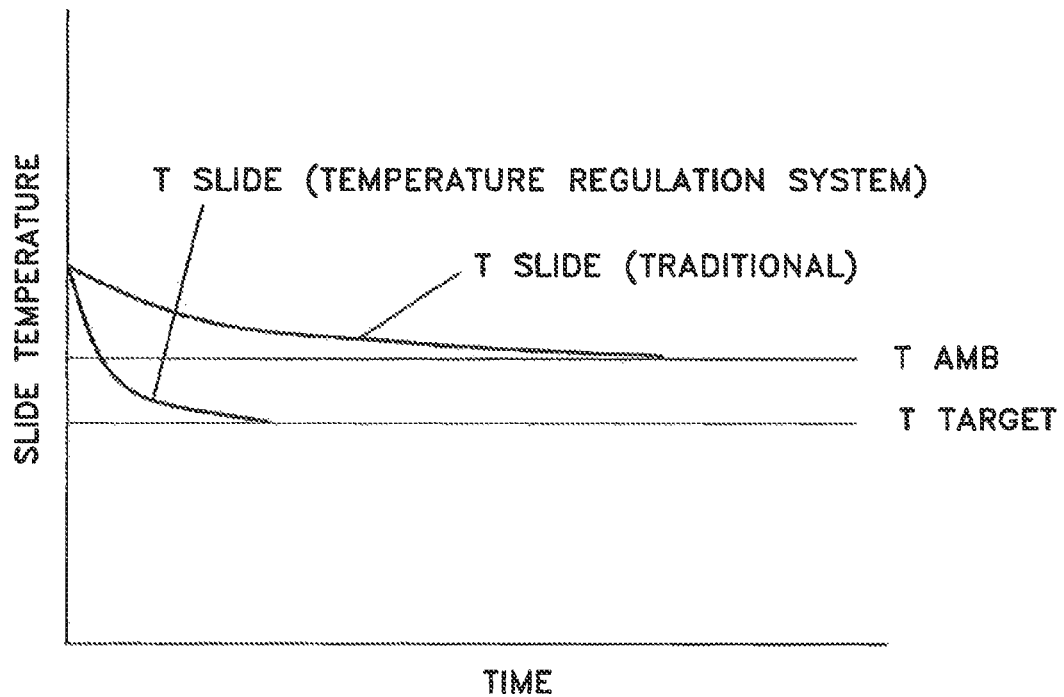
FIG. 12 is a comparison chart of exemplary temperature changes for an embodiment of the present invention and potential temperature changes of a traditional system in relation to a protocol temperature target, wherein ambient system and sample carrier temperatures may be initially above the protocol temperature target.
Figure 13:
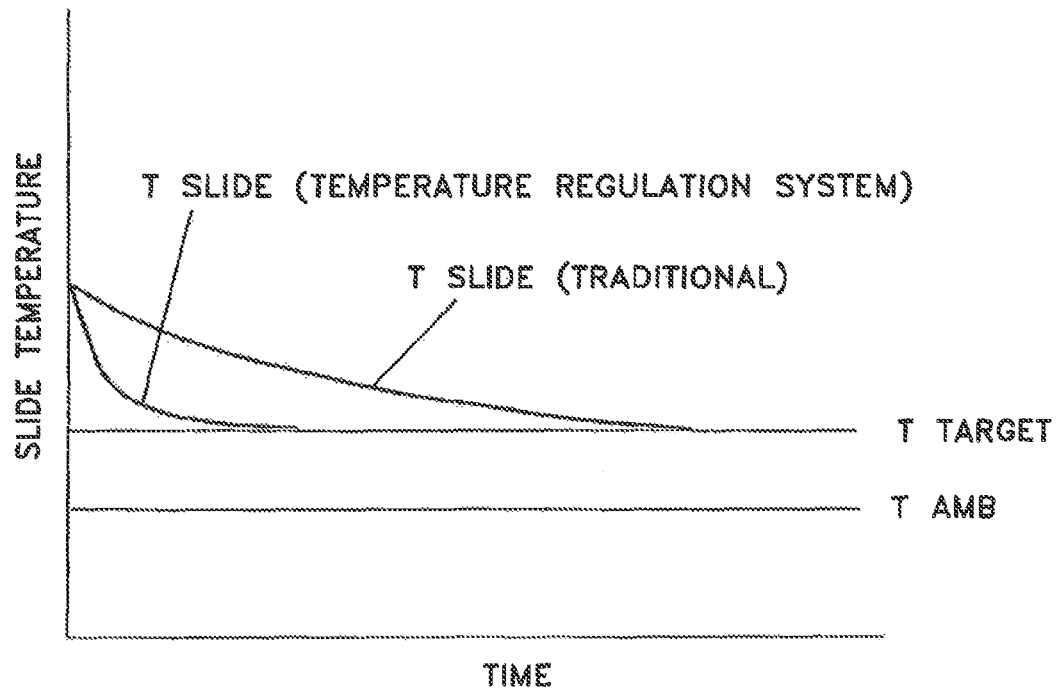
FIG. 13 is a comparison chart of exemplary temperature changes for an embodiment of the present invention and potential temperature changes of a traditional system in relation to a protocol temperature target, wherein sample carrier temperature may be initially above the protocol temperature target and ambient system temperature may be below the protocol temperature target.

The various embodiments of the disclosed temperature regulation system and the sample processing control system feature the capability to control system temperature, and in some embodiments, slide temperature and reagent temperature. The combination of features may allow active heating and cooling of sample carriers, and in some embodiments potentially utilizing a controlled Peltier device or temperature control, a conductive device or temperature control, or a combination of temperature control features. One preferred temperature control sequence may allow a controlled (e.g., adjustment or maintenance within a particular set parameters such as rate of change or the like) or even accelerated increase and/or decrease in slide temperature, perhaps including independently a ramping up and/or down of the temperature. The system may be considered as including a controlled temperature element or a controlled active temperature element, such as a controlled active temperature reduction element or the like. Another example of a controlled temperature sequence is shown in FIGS. 12 and 13. These figures generally illustrate and compare temperature changes of the present invention and a type of traditional system. They illustrate target temperature tolerance, the time necessary to reach values, and ambient temperature aspects. In some embodiments, energy may be delivered at the same or about the same rate by the temperature regulation system as a traditional system. Energy may also, however, be removed or added, and perhaps even removed or added faster or slower than a traditional system, as traditional systems may dissipate energy to the ambient. A shorter or longer period for temperature effects, such as sample carrier cooling, may result. Active temperature regulation, in some embodiments heating and cooling, may be provided in some embodiments to provide such results.

In some embodiments, when a temperature disturbance greater than the target temperature occurs, such as by the effect of warm sample carriers, the present invention may rely on a conductive temperature regulation system, such as a substrate temperature regulation device, so as to dissipate excess energy, as previously described.

The temperature may be controlled within the required temperature tolerance for the sequence and controlled to maintain lesser values of rates of temperature change (dT/dt) during the sequence. The temperature range for a slide processed in accordance with conventional processing may exhibit greater values of rates of temperature change and may have temperatures beyond required tolerances for a significant portion of a sequence. As a result, the uncontrolled temperatures may be detrimental to the outcome for a protocol, such as the staining example previously described in relation to traditional technologies. An excessive low or high ambient temperature, and particularly an uncontrolled temperature, may cause a slower rate of temperature change and therefore may require a longer time to reach a desired temperature value as may be required by the protocol.

Figure 14:
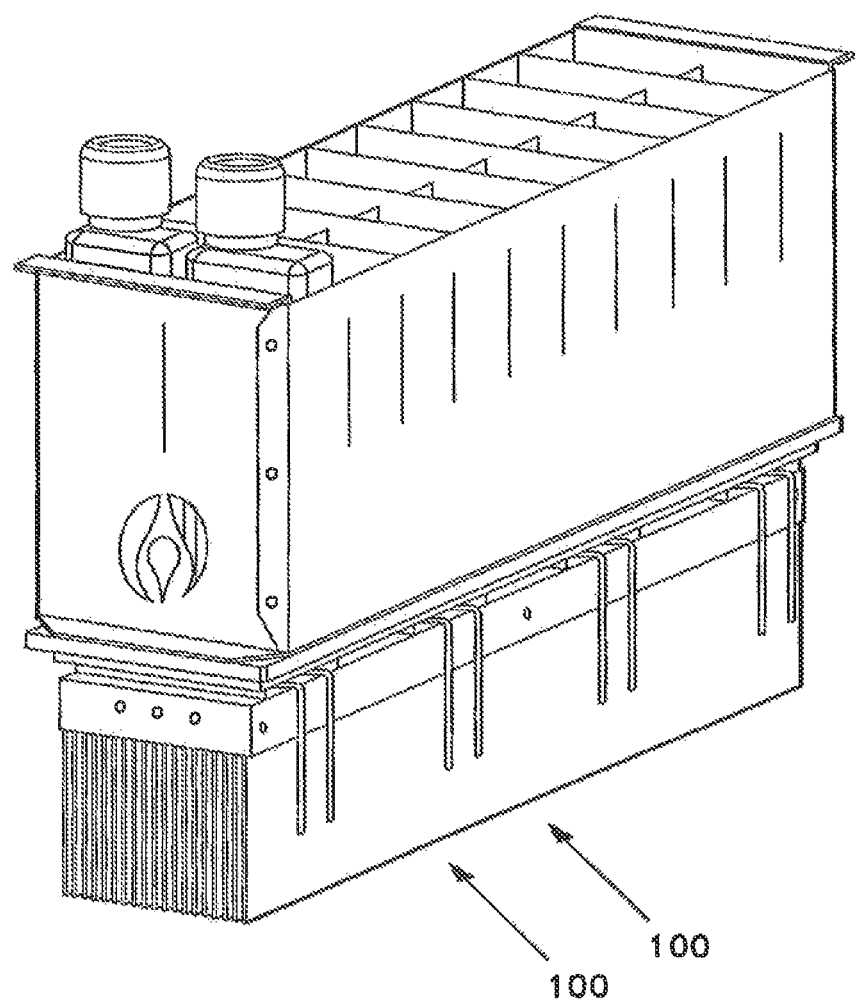
FIG. 14 is an isometric perspective view of an embodiment of reagent container temperature control aspects of an embodiment of the invention.

The various embodiments of the disclosed temperature regulation system may feature the capability of controlling reagent temperature alone or in addition to sample temperature. One embodiment of a reagent temperature regulation system is shown in FIG. 14 and may include a conduction temperature regulation system. A reagent temperature regulation system may have conductive regulation elements 100 perhaps mounted below the reagent tray. The conductive regulation elements may feature thermoelectric regulation features such as Peltier-type temperature regulation. Naturally, a sensing element may be provided as part of arm 20 or in another sample processing configuration, may be incorporated to sense temperature, perhaps instantaneously. This may assist in maintaining temperature tolerances and in controlling rates of temperature change. Photodiode devices, electric conductivity devices, IR sensors, sensors acting through septa of a container, or other sensors may be included to sense values such as reagent containers or slides collectively or individually.

Temperature control of the temperature regulation system may be provided to take advantage of the active heating and cooling capability of the above described temperature regulation system. Accordingly, in some embodiments temperature control may be provided to at least actively regulate temperature within protocol tolerances. The temperature regulation system of the present invention previously described may be accordingly configured to increase or reduce temperature, and in some embodiments actively increase or reduce temperature. The adaptive sample processing control system may provide a corresponding controlled increase or reduction of temperature, and in some embodiments actively controlled increase or reduction of temperature. It may also reduce the rate of an increase or decrease in temperature change (as compared to the often-used maximum power type of approach) such as by intermittently powering or lower powering the device or the like and may thus provide a reduced rate of temperature change element. Corresponding methods of the invention may comprise methods of temperature control of sample processing systems, comprising the step of regulating, temperature within protocol tolerances, and in some embodiments, actively regulating temperature. Further methods of temperature control of sample processing systems are disclosed comprising one or more steps of actively increasing temperature, actively reducing temperature, or a combination of such steps. A method of temperature control of sample processing systems is further disclosed comprising the step of controlling increase of temperature, controlling reduction of temperature, or a combination of such steps. Corresponding methods of the invention relate to temperature control of samples, sample carriers, and reagents.

Figure 7:
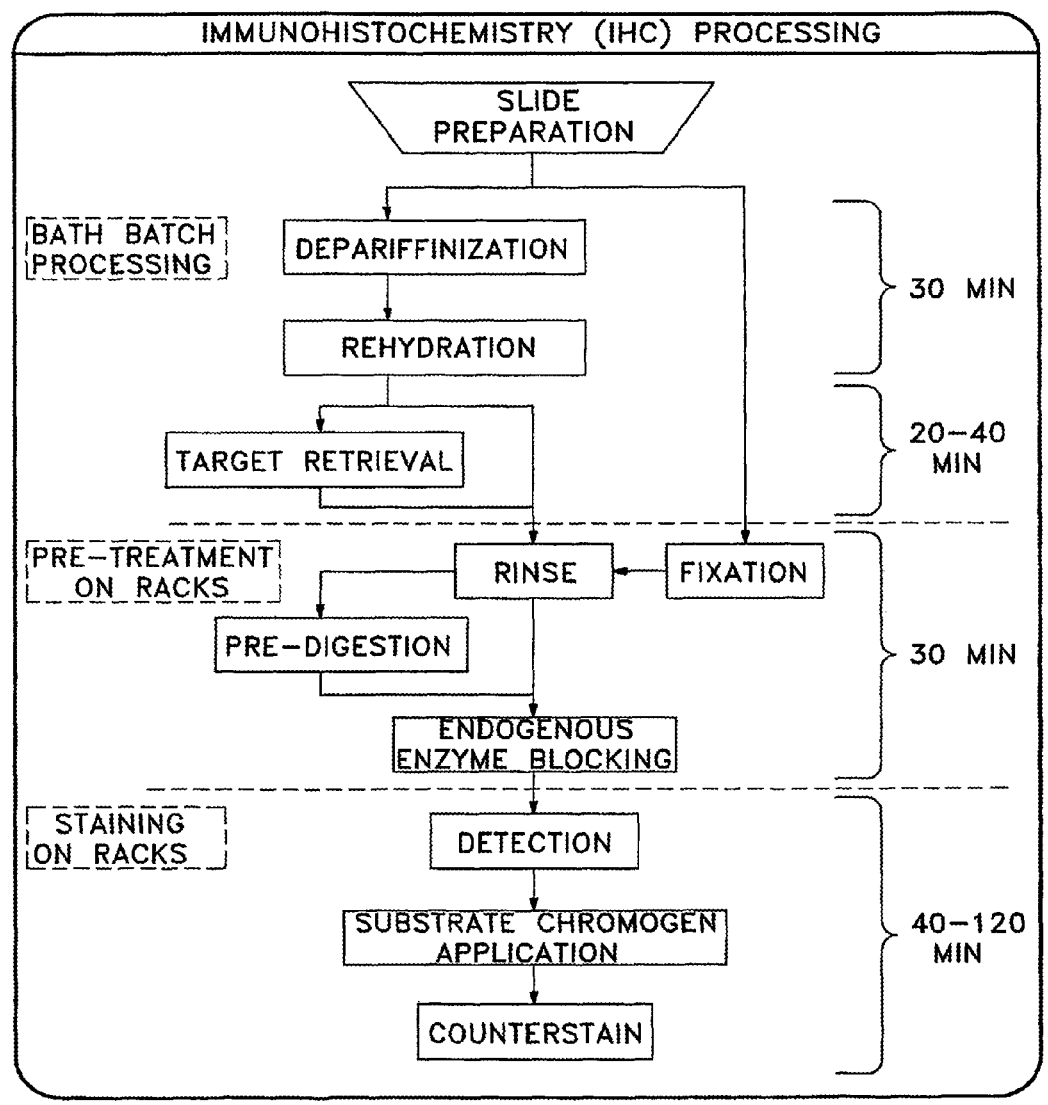
FIG. 7 is a flow chart of some representative process steps of an embodiment of the invention.

The processing of samples may be accomplished according to sequences perhaps such as shown in FIGS. 7 and 8. These are but one example, and of course, variants of these protocols and processing steps will exist for any given sample. One processing sequence may broadly comprise the pre-processing of a sample, if needed, such as deparaffinization (as previously described), and may further comprise target retrieval (as previously described), and sample staining.

As shown in FIG. 9, control of the processing samples may be accomplished with a sample processing system manager 500, such as a computer server connected with one or more sample processing systems. Connection among perhaps a number of process systems and perhaps a number of computers, such as workstations and a server (the latter residing either separately or as part of a workstation), may be achieved by use of a local area network (LAN), such as a group of computers and associated devices that share a common communications line or perhaps wireless link and may even share the resources of a single processor, memory, or server within a small geographic area (for example, within an office building or complex). Connection may also be established to a laboratory network, facilities intranet system, or even a laboratory information system such as through a bridge. Temperature values, historical actions, and particular timing activities may be captured and stored for local or remote access through the use of such a system.

In some embodiments, specifics of in-situ hybridization (ISH) may be addressed. Embodiments of ISH may require a small volume of agent, such as 15 micro liters, to be placed on the sample. Heat control may be maintained between about 95-100° C. comprises and kept constant for a period of time. Temperature may then be lowered in a controlled manner.

As can be easily understood from the foregoing, the basic concepts of the present invention may be embodied in a variety of ways. It involves both sample processing techniques as well as various systems, assemblies, and devices to accomplish sample processing and other functions. In this application, the sample processing techniques are also disclosed as part of the results shown to be achieved by the various systems, assemblies, and devices described and as steps which are inherent to utilization. They should be understood to be the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

Further, each of the various elements and features of the invention and claim may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "retention element" should be understood to encompass disclosure of the act of "retaining"—whether explicitly discussed or not—and, conversely, were there effectively disclosure of the act of "retaining", such a disclosure should be understood to encompass disclosure of a "retention element" and even a "means for retaining". It should also be understood that in jurisdictions where specific language may be construed as limiting, as but one example in the United States where some interpretations of "means for" elements can be construed narrowly, broader equivalent language (such as "element" or the like) may be used and should be understood as encompassed by this specification. Such changes and alternative terms are to be understood to be explicitly included in the description.

Any acts of patents, patent applications, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, any priority case for this application is hereby appended and hereby incorporated by reference.

Further, if or when used, the use of the transitional phrase "comprising" or the like is used to maintain the "open-end" claim herein, according to traditional claim interpretation. Thus, unless the context requires otherwise, it should be understood that the term "comprise" or variations such as "comprises" or "comprising" or the like, are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claim set forth at any time are hereby incorporated by reference as part of this description of the invention, and the applicant expressly reserves the right to use all of or a portion of such incorporated content of such claim as additional description to support any of or all of the claim or any element or component thereof, and the applicant further expressly reserves the right to move any portion of or all of the incorporated content of such claim or any element or component thereof from the description into the claim or vice-versa as necessary to define the matter for which protection is sought by this application or by any subsequent continuation, division, or continuation-in-part application thereof, or to obtain army benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for the automated processing of at least one sample on at least one carrier according to a processing protocol, comprising:

inserting at least one reagent container to a position within a reagent section where it remains until the at least one reagent container is exchanged;

inserting at least one carrier to a position in at least one carrier section where it remains until processing of the sample on the carrier is completed;

regulating the temperature of the at least one sample via an active temperature regulation element to a set point and within a tolerance specified by the protocol;

dispensing fluid on the at least one carrier via a moveable robotic member according to the processing protocol;

monitoring the at least one carrier;

controlling the moveable robotic member according to the processing protocol; and exchanging the at least one reagent container and the at least one carrier during the processing protocol without interrupting the fluid dispensing of the robotic member.

2. The automated processing method of claim 1, wherein the processing protocol includes immunohistochemistry processing steps.

3. The automated processing method of claim 1, wherein the processing protocol includes in-situ hybridization processing steps.

4. The automated processing method of claim 1, wherein the processing protocol includes automated fluorescent in-situ hybridization processing steps.

5. The automated processing method of claim 1, wherein the processing protocol includes automated microarray processing steps.

6. The automated processing method of claim 1, wherein the processing protocol includes target retrieval processing steps.

7. The automated processing method of claim 1, wherein the processing protocol is performed by an automated stainer processing system.

8. The automated processing method of claim 1, wherein said active temperature regulation element comprises a temperature reduction element.

9. The automated processing method of claim 8, wherein said temperature reduction element comprises a controlled active temperature reduction element.

10. The automated processing method of claim 8, wherein said temperature reduction element maintains said sample at less than an ambient temperature.

11. The automated processing method of claim 1, wherein said active temperature regulation element comprises a temperature ramp up element.

12. The automated processing method of claim 1, wherein said active temperature regulation element comprises a temperature ramp down element.

13. The automated processing method of claim 1, wherein said active temperature regulation element causes both a regulated temperature increase and a regulated temperature decrease of said sample.

14. The automatic processing method of claim 7, further comprising establishing a network connection between the automated stainer processor system and at least one computer.

15. The automatic processing method of claim 14, wherein the at least one computer is a server and wherein the stainer is a client of the server.

16. The automatic processing method of claim 14, further comprising establishing a network connection between the at least one computer and a second automated stainer processing system.

17. The automatic processing method of claim 14, wherein the at least one computer is connected to a laboratory information system.

18. The automatic processing method of claim 14, wherein at least one of temperature values, historical actions, and particular timing activities are stored for remote access by the at least one computer.

19. A method for the automated processing of at least one sample on at least one carrier according to a processing protocol, comprising:

inserting at least one reagent container to a position within a reagent section where it remains until the at least one reagent container is exchanged;

inserting at least one carrier to a position in at least one carrier section where it remains until processing of the sample on the carrier is completed;

regulating the temperature of the at least one sample via an active temperature regulation element to a set point and within a tolerance specified by the protocol;

dispensing fluid on the at least one carrier via a moveable robotic member according to the processing protocol;

monitoring the at least one carrier;

controlling the moveable robotic member according to the processing protocol; and exchanging the at least one reagent container during the processing protocol without interrupting the fluid dispensing of the robotic member.

20. A method for the automated processing of at least one tissue sample on a microscopic slide according to a processing protocol, comprising:

inserting at least one reagent container to a position within a reagent section of an automated stainer where it remains until the at least one reagent container is exchanged;

inserting at least one sample on a microscopic slide to a position within in at least one carrier section of the automated stainer where it remains until processing of the sample is complete;

regulating the temperature of the at least one sample via an active temperature regulation element to a set point and within a tolerance specified by the protocol;

dispensing fluid on the at least one microscopic slide via a moveable robotic member according to the processing protocol;

monitoring the at least one microscopic slide;

controlling the moveable robotic member according to the processing protocol; and exchanging the at least one microscopic slide from the at least one carrier section in which it is positioned with a second at least one microscopic slide during the processing protocol without interrupting the fluid dispensing of the robotic member.

* * * * *